US00PP19161P3

(12) United States Plant Patent
Austin

(10) Patent No.: US PP19,161 P3
(45) Date of Patent: Aug. 26, 2008

(54) ***ROSA HYBRIDA* SHRUB NAMED 'AUSGLADE'**

(50) Latin Name: *Rosa hybrida*
Varietal Denomination: AUSglade

(75) Inventor: David C. H. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 0 days.

(21) Appl. No.: 11/904,126

(22) Filed: Sep. 26, 2007

(65) Prior Publication Data

US 2008/0141394 P1 Jun. 12, 2008

(30) Foreign Application Priority Data

Nov. 13, 2006 (EP) ..... 2006/2287

Feb. 16, 2007 (KE) ..... ROS 07 833

(51) Int. Cl.
*A01H 5/00* (2006.01)

(52) U.S. Cl. ..... Plt./107

(58) Field of Classification Search ..... Plt./107
See application file for complete search history.

*Primary Examiner*—Annette H Para
*Assistant Examiner*—S. B. McCormick-Ewoldt
(74) *Attorney, Agent, or Firm*—Kauth, Pomeroy, Peck & Bailey LLP

(57) ABSTRACT

A variety of rose plant of the shrub class, named 'AUSglade' suitable for cut flower production is disclosed. The 'AUSglade' rose is a plant suitable for year round production under standard greenhouse conditions having deep pink blooms with a strong myrrh fragrance and long vase life, which are produced on strong upright stems.

1 Drawing Sheet

Classification: The present invention relates to a new *Rosa hybrida* shrub.

Variety denomination: The new plant has the varietal denomination 'AUSglade'.

ORIGIN OF INVENTION

This invention relates to a new and distinct variety of shrub rose plant named 'AUSglade', which was originated by crossing two unnamed, unpatented varieties of *Rosa hybrida.*

BACKGROUND OF THE INVENTION

The primary objective of this breeding was to produce a plant suitable for year round production under standard greenhouse conditions having deep pink blooms with a strong myrrh fragrance and long vase life, which are produced on strong upright stems.

SUMMARY OF THE INVENTION

Among the features which distinguish the new variety from other presently available and commercial rose cultivars known to the inventor is the following combination of characteristics: deep pink blooms with a strong myrrh fragrance and a long vase life. The plant has a strong upright stem, which makes it suitable for year round cut flower production under standard greenhouse conditions.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSglade' may be asexually propagated by budding and grafting. The budding and grafting successfully occurred on the plant/rootstock *Rosa* cv. 'Natal Briar'.

COMPARISON WITH PARENTS

The new rose may be distinguished from its seed parent, by the following combination of characteristics: whereas the parent has red blooms with a pale reverse, 'AUSglade' bears flowers of deep pink. The new variety is classified as a *hybrida* rose with a strong upright growing habit.

The new variety may be distinguished from its pollen parent, by the following combination of characteristics: whereas the pollen parent bears red blooms, 'AUSglade' bears flowers of a deep pink. In addition, the new variety bears blooms that are quartered, whereas the pollen parent bears blooms that are rosette shaped.

COMPARISON WITH THE CLOSEST COMMERCIALLY AVAILABLE CULTIVAR

The closest commercially available cultivar to the new variety is the 'AUSimmon' (U.S. Pat. No. 17,267). The new rose may be distinguished from the 'AUSimmon' variety by the following combination of characteristics: the 'AUSimmon' has fewer petals, medium pink blooms and more prickles compared to 'AUSglade', which has a greater number of petals, pink to mauve blooms and fewer prickles.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

The following description is of 2 year-old rose plants of the new variety grown outdoors in Albrighton, Britain in the month of August. Phenotypic expression may vary with environmental, cultural and climatic conditions, as well as differences in conditions of light and soil.

Flower characteristics:

*Blooming habit.*—Continuous. The number of blooms per plant during the growing season is profuse, but there are too many to count.

*Bud.*—Size: About 3.5 cm long and 2.3 cm in diameter when the petals start to unfurl. Form: The bud form is pointed ovoid. Color: When sepals first divide, the bud color is Red Group 53B. When half blown, the upper sides of the petals are Red-Purple Group 68B with Red-Purple Group N66C at base and the lower sides of the petals are Red-Purple Group N66C in the top third, the rest being Red-Purple Group N66A. Calyx: Shape: irregularly rounded. Length: 4 cm. Diameter: 3.5 cm.

*Sepals.*—Arrangement: Regular. Color: Upper Surface: Yellow-Green Group 146C. Lower Surface: Yellow-Green Group 144A overlaid with Greyed-Purple Group 184A. Length: 4.1 cm. Width: 1–1.1 cm. Shape: Subulate. Margin: Slightly canescent. Surface texture: Upper Surface: Pubescent. Lower Surface: Smooth. Number: There are three lightly appendaged sepals. There are 2 unappendaged sepals with hairy edges.

*Receptacles.*—Color: Yellow-Green Group 144B. Shape: other campanulate. Size: medium, about 1.2 cm×1.3 cm. Surface: Smooth.

*Peduncle.*—Length: long, averaging about 8 cm. Surface: prickly. Color: Yellow-Green Group 144A. Strength: Strong.

*Blooms.*—Size: Large, average open diameter is about 11.2 cm. Borne: Singly in clusters of 5–6 (buds are nipped out to leave a single bloom) blooms having corymb shaped inflorescence. Stems: Strength: Strong, average length is about 45–50 cm. Diameter: 6 mm. Form: When first open, bloom is cupped. Permanence of bloom: Retains its form to the end outer petals curl back.

*Petalage.*—Number of petals under normal conditions: 140–150. Color: The upper sides of the petals are Red-Purple Group N66B. The reverse sides of the petals are Red-Purple Group N66D (veins clearly visible—Red-Purple Group N66C). The base of the petals is Red-Purple Group N66C. Fragrance: Strong. Character of fragrance: Myrrh.

*Petals.*—Texture: Smooth, satiny, thick. Size: Width: 3.5 cm. Length: 3.8 cm. Surface: Smooth. Shape: Obovate. Margin: Entire. Apex Shape: Some obtuse, some cuspidate. Base Shape: Outer petals are rounded, inner petals cuneate. Form: Incurved; tips of outer petals recurved. Arrangement: Quartered. Petaloids: Number: 7. Color: Petal: Red-Purple Group N66A: Anther, Yellow-Orange Group 23C; Filament: Yellow Group 8B. Length: Petal: 8 mm. Anther: 2 mm. Filament: 5 mm. Width: Petal only: 2 mm. Shape: Irregular. Margin: Irregular. Persistence: Petals drop off cleanly before drying. Lastingness: On the plant: long, about 12 days. As a cut flower: fair, about 10 days.

*Reproductive parts.*—Stamens: Number: 70–75. Length: 5–6 mm. Anthers: Length: 2 mm. Color: Yellow-Orange Group 23B. Arrangement: Regular around styles mixed with petaloids. Filaments: Color: Yellow Group 10B. Length: 3–4. Pollen: Color: Yellow-Orange Group 23B. Pistils: Number: 80–90. Length: 10 mm. Styles: Color: Yellow Group 2D. Length: 9 mm. Stigmas: Color: Yellow Group 2C. Length: 1 mm. Hips: None Observed.

Plant characteristics:

*Plant form.*—Shrub (grown solely for cut flower production).

*Plant growth.*—Vigorous and upright.

*Age to maturity.*—Two years.

*Mature plant.*—Height: 1.6 m. Width: 0.8 m.

*Rootstock.*—*Rosa* 'Natal Briar' for the observed plants.

*Foliage.*—Number: Leaflets on normal mid-stem leaves is: 5–7 (including terminal leaflet). Size: Medium, about 15.5 cm long×12.4 cm wide. Quantity: Normal. Number of leaves per flowering stem is: 10–12. Color: New foliage: Upper side: Yellow-Green Group 146A with Greyed-Purple Group 183B around margin. Lower side: Yellow-Green Group 146A overlaid with Greyed-Purple Group 183B. Old foliage: Upper side: Green Group 139A. Lower side: Yellow-Green Group 147B.

*Leaflets.*—Size: About 8.5 cm long×4.6 cm wide. Shape: Pointed oval. Base Shape: Some rounded, some cuneate. Apex Shape: Acuminate. Texture: Smooth. Edge: Serrated. Serrations: Single large. Petiole: Color: Yellow-Green Group N144C. Length: 4–5 cm. Width: 2 mm. Surface Texture: Prickly. Petiole Rachis: Color: Yellow-Green Group N144C. Underside: with prickles. Stipules: Length: 2 cm, (slightly) serrated/glandular. Color: Green Group 143A. Auricle: Shape: Falcate. Length: 6–10 mm. Width: 1–2 mm at base tapering to point in final third. Color: Green Group 143A. Vein Color: Yellow-Green Group N144D. Venation Pattern: Reticulate.

*Wood.*—New Wood: Color: Yellow-Green Group 148A overlaid with Greyed-Purple Group 185B. Bark: Smooth. Old Wood: Color: Green Group 138A. Bark: Smooth.

*Branching habit.*—Lateral Branch Dimensions: Length: 45 cm. Diameter: 6 mm.

*Stems.*—Mature Stem: Length: 45–50 cm. Diameter: 6 mm. The above measurements are all variable, depending on growing conditions in a season. Stem Pubescence Present: No.

*Prickles.*—Quantity: On main canes from base: ordinary. Number per stem length: 8–10 per 10 cm. On laterals from main canes: ordinary. Number per stem length: 10 per 10 cm. Form: Concave curved inward. Length: 1–1.6 mm. Color when young: Yellow-Green Group 153A overlaid with Red Group 46A, more concentrated near tip and margin. Color when mature: Greyed-Orange Group 165B.

*Small prickles.*—Quantity: Main stalk: Few. Number per stem length: 15 per 10 cm. Laterals: None. Color: When young: Yellow-Green Group 153A. When mature: Greyed-Orange Group 165B.

*Disease resistance.*—Mildew: Resistant. Blackspot: Resistant. Rust: Resistant.

*Pest resistance.*—Not tested.

*Winter hardiness.*—Not tested.

*Growing conditions.*—Special. Greenhouse rose for cut flower production; disbud where necessary to leave one bloom per stem.

What is claimed is:

1. A new and distinct variety of rose plant of the shrub class suitable for cut flower production in greenhouse conditions, substantially as herein shown and described.

* * * * *

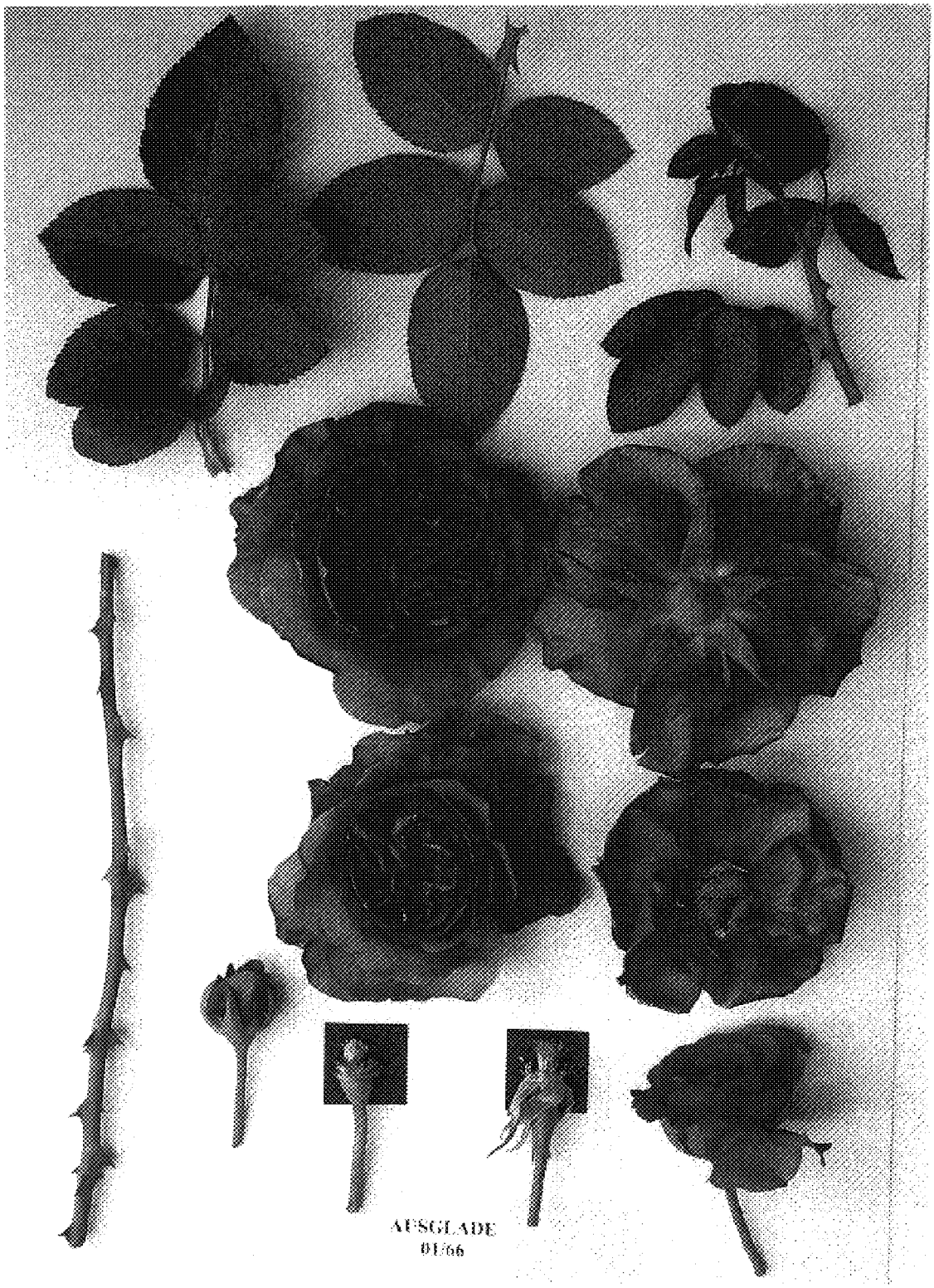
AUSGLADE
01/66